United States Patent [19]

Goulmy et al.

[11] Patent Number: 5,770,201
[45] Date of Patent: Jun. 23, 1998

[54] HA-2 ANTIGENIC PEPTIDE

[75] Inventors: Els A. J. M. Goulmy, Oegstgeest, Netherlands; Donald F. Hunt; Victor H. Engelhard, both of Charlottesville, Va.

[73] Assignee: Rijsuniversiteit Te Leiden, Leiden, Netherlands

[21] Appl. No.: 363,691

[22] Filed: Dec. 23, 1994

[51] Int. Cl.⁶ ............................ A61K 39/00; C07K 14/78
[52] U.S. Cl. .................................. 424/185.1; 424/277.1; 530/300; 530/328; 530/395; 530/868
[58] Field of Search ............................ 424/185.1, 277.1; 530/350, 395, 300, 328, 868

[56] References Cited

PUBLICATIONS

Bortin, M.M., "A Compendium of Reported Human Bone Marrow Transplants," (1970) *Transplantation* 9, 571–587.
Bortin, M.M. et al., "Progress in Bone Marrow Transplantation for Leukemia: A Preliminary Report from the Advisory Committee of the International Bone Marrow Transplant Registry," (1991) *Transplant. Proc.* 23, 61–62.
Beatty, P.G. and Hervé, P., "Immunogenetic Factors Relevant to Human Acute Graft–vs.–Host Disease," (1989) In *Graft–versus Host Disease: Immunology, Pathophysiology, and Treatment,* 415–423.
Beatty, P.G. et al, "Marrow Transplantation from HLA––matched Unrelated Donors for Treatment of Hematologic Malignancies," (1997) *Transplantation* 51, 443–447.
Martin, P.J., "Increased Disparity for Minor Histocompatibility Antigens as a Potential Cause of Increased GVHD Risk in Marrow Transplantation from Unrelated Donors Compared with Related Donors," (1991) *Bone Marrow Transplant.* 8(3), 217–223.
Goulmy, E. et al., "A Minor Transplantation Antigen Detected by MHC–Restricted Cytotoxic T Lymphocytes During Graft–Versus–Host Disease," (1983) *Nature* 302(5904), 159–161.
Tsoi, M.–S. et al., "Cell–Mediated Immunity to Non–HLA Antigens of the Host by Donor Lymphocytes in Patients with Chronic Graft–vs–Host Disease," (1980) *J. Immunol.* 125, 2258–2262.
Tsoi, M.–S. et al., "Anti–host Cytotoxic Cells in Patients with Acute Graft–versus–Host Disease After HLA–Identical Marrow Grafting," (1983) *Transplant. Proc.* 15, 1484–1486.
Irle, C. et al., "Alloreactive T Cell Responses between HLA–Identical Siblings," (1985) *Transplantation* 40(3), 329–333.
van Els, C.A. et al., "Effector Mechanisms in Graft–versus––Host Disease in Response to Minor Histocompatibility Antigens.I. Absence of Correlation with Cytotoxic Effector Cells," (1990) *Transplantation* 50(1), 62–66.
Irschick, E.U. et al., "Studies on the Mechanism of Tolerance of Graft–versus–Host Disease in Allogeneic Bone Marrow Recipients at the Level of Cytotoxic T–Cell Precursor Frequencies," (1992) *Blood* 79(6), 1622–1628.

Niederwieser, D. et al., "Correlation of Minor Histocompatibility Antigen–Specific Cytotoxic T Lymphocytes with Graft–Versus–Host Disease Status and Analyses of Tissue Distribution of Their Target Antigens," (1993) *Blood* 81(8), 2200–2208.
van Els, C.A. et al., "Immunogenetics of Human Minor Histocompatibility Antigens: Their Polymorphism and Immunodominance," (1992) *Immunogenetics* 35(3), 161–165.
Schreuder, G.M. et al., "A Genetic Analysis of Human Minor Histocompatibility Antigens Demonstrates Mendelian Segregation Independent of HLA," (1993) *Immunogenetics* 38(2), 98–105.
de Bueger, M. et al., "Tissue Distribution of Human Minor Histocompatibility Antigens. Ubiquitous versus Restricted Tissue Distribution Indicates Heterogeneity Among Human Cytotoxic T Lymphocyte–Defined non–MHC Antigens," (1992) *J. Immunol* 149(5), 1788–1794.
van der Harst, D. et al., "Recognition of Minor Histocompatibility Antigens on Lymphocytic and Myeloid Leukemic Cells by Cytotoxic T–Cell Clones," (1994) *Blood* 83(4), 1060–1066.
Wallny, H.–J. et al., "Identification of Classical Minor Histocompatibility Antigen as Cell–Derived Peptide," (1990) *Nature* 343(6255), 275–278.
Rötzschke, O. et al., "Characterization of Naturally Occurring Minor Histocompatibility Peptides Including H–4 and H–Y," (1990) *Science* 249(4966), 283–287.
Sekimata, M. et al., "Isolation of Human Minor Histocompatibility Peptides," (1992) *Int. Immunol* 4(2), 301–304.
Franksson, L. et al., "Immunization Against Tumor and Minor Histocompatibility Antigens by Eluted Cellular Peptides Loaded on Antigen Processing Defective Cells," (1993) *Eur.J.Immunol* 23(10), 2606–2613.
Loveland, B. et al., "Maternally Transmitted Histocompatibility Antigen of Mice: a Hydrophobic Peptide of a Mitochondrially Encoded Protein," (1990) *Cell* 60(6), 971–980.
Goulmy, E., "Minor Histocompatibility Antigens and Their Role in Transplantation," (1988) *Transplantation Reviews* 2, 29–54.
de Bueger, M. et al., "Isolation of an HLA–A2.1 Extracted Human Minor Histocompatibility Peptide," (1993) *Eur. J. Immunol* 23(3) 614–618.

(List continued on next page.)

*Primary Examiner*—Thomas M. Cunningham
*Attorney, Agent, or Firm*—Hoffman & Baron, LLP

[57] ABSTRACT

The present invention discloses the first peptide sequence of a so called minor H antigen, The minor H antigens are associated with the Graft-versus-Host Disease. The peptide and its derivatives find many uses in bone marrow transplantation, organ transplantation and in the treatment of leukemia. The peptide and its derivatives can be incorporated in vaccines, in pharmaceutical formulations and they can be used in diagnostic test kits. The peptide is derived from the HA-2 minor antigen and has the sequence YXGEV-XVSV (SEQ ID NO: 1), wherein X represents a leucine or an isoleucine residue. Both donors and recipients in bone marrow transplantation can be treated with the peptides, optionally in combination with other peptides, coupled to carriers, with suitable excipients and/or adjuvants.

11 Claims, 9 Drawing Sheets

OTHER PUBLICATIONS

Kurtz, M.E. et al., "CTL and Serologically Defined Antigens of B2m,H–3 Region," (1985) *J. Immunol.* 135(4), 2847–2852.

Rammensee, H.-G. et al., "Restricted Recognition of $\beta_2$–Microglobulin by Cytotoxic T Lymphocytes," (1986) *Nature* 319(6053), 502–504.

Pérarnau, B. et al., "$\beta_2$–Microglobulin Restriction of Antigen Presentation," (1990) *Nature* 346, 751–754.

Cox, A.L. et al., "Identification of a Peptide Recognized by Five Melanoma–Specific Human Cytotoxic T Cell Lines," (1994) *Science* 264, 716–719.

Udaka, K. et al., "A Naturally Occuring Peptide Recognized by Alloreative CD8+ Cytotoxic T Lymphocytes in Association with a Class I MHC Protein," (1992) *Cell* 69, 989–998.

Henderson, R.A. et al., Direct Identification of an Endogenous Peptide Recognized by Multiple HLA–A2.1 Specific Cytotoxic T Cells,: (1993) *Proc. Natl. Acad. Sci. U.S.A.* 90, 10275–10279.

Mandelboim, O. et al., "CTL Induction by a Tumor Associated Antigen Octapeptide Derived from a Murine Lung Carcinoma," (1994) *Nature* 369, 67–71.

Uenaka, A. et al., "Identification of a Unique Antigen Peptide pRL1 on BALB/c RL♂1 Leukemia Recognized by Cytotoxic T Lymphocytes and its Relation to the *Akt* Oncogene," (1994) *J. Exp. Med.* 180, 1599–1607.

Chen, Y. et al., "Naturally Processed Peptides Longer than Nine Amino Acid Residues Bind to the Class I MHC Molecule HLA–A2.1 with High Affinity and in Different Conformations," (1994) *J. Immunol.* 152(6), 2874–2881.

Ruppert, J. et al., "Prominent Role of Secondary Anchor Residues in Peptide Binding to HLA–A2.1 Molecules," (1993) *Cell* 74(5), 929–937.

Huczko, E.L. et al., "Characteristics of Endogenous Peptides Eluted from the Class I MHC Molecule HLA–B7 Determined by Mass Spectrometry and Computer Modeling," (1993) *J. Immunol.* 151, 2572–2587.

Titus, M.A., "Myosins," (1993) *Curr. Opin. Cell Biol.* 5, 77–81.

Coudrier, E. et al., "Do Unconventional Myosins Exert Functions in Dynamics of Membrane Compartments?," (1992) *FEBS Letters* 307(1), 87–92.

Mooseker, M., "A Multitude of Myosins," (1993) *Curr. Biol.* 3, 245–248.

Bement, W.M., "Cloning and mRNA Expression of Human Unconventional Myosin–IC. A Homologue of Amoeboid Myosins–I with a Single IQ Motif and a SH3 Domain," (1994) *J. Mol. Biol.* 243, 356–363.

Bement, W.M. et al., "Identification and Overlapping Expression of Multiple Unconventional Myosin Genes in Veterbrate Cell Types," (1994) *Proc. Natl. Acad. Sci. U.S.A.* 91, 6549–6553.

Falk, K. et al., "Allele–specific Motifs Revealed by Sequencing of Self–Peptides Eluted from MHC Molecules," (1991) *Nature* 351, 290–296.

Hunt, D.F. et al., "Characterization of Peptides Bound to the Class I MHC Molecule HLA–A2.1 by Mass Spectrometry," (1992) *Science* 255, 1261–1263.

Hunt, D.F. et al., "Protein Sequencing by Tandem Mass Spectrometry," (1986) *Proc. Natl. Acad. Sci. U.S.A.* 83, 6233–6237.

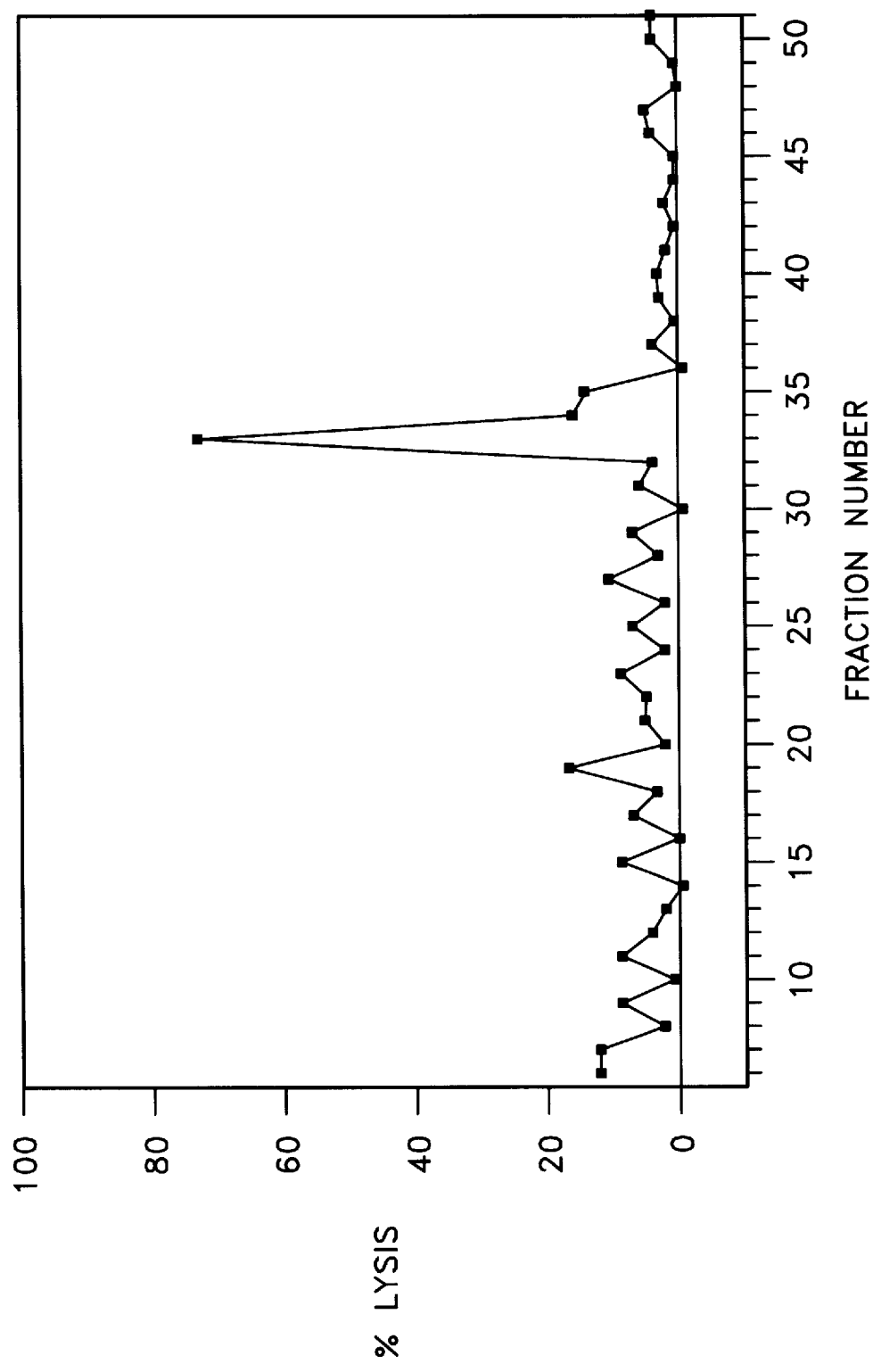

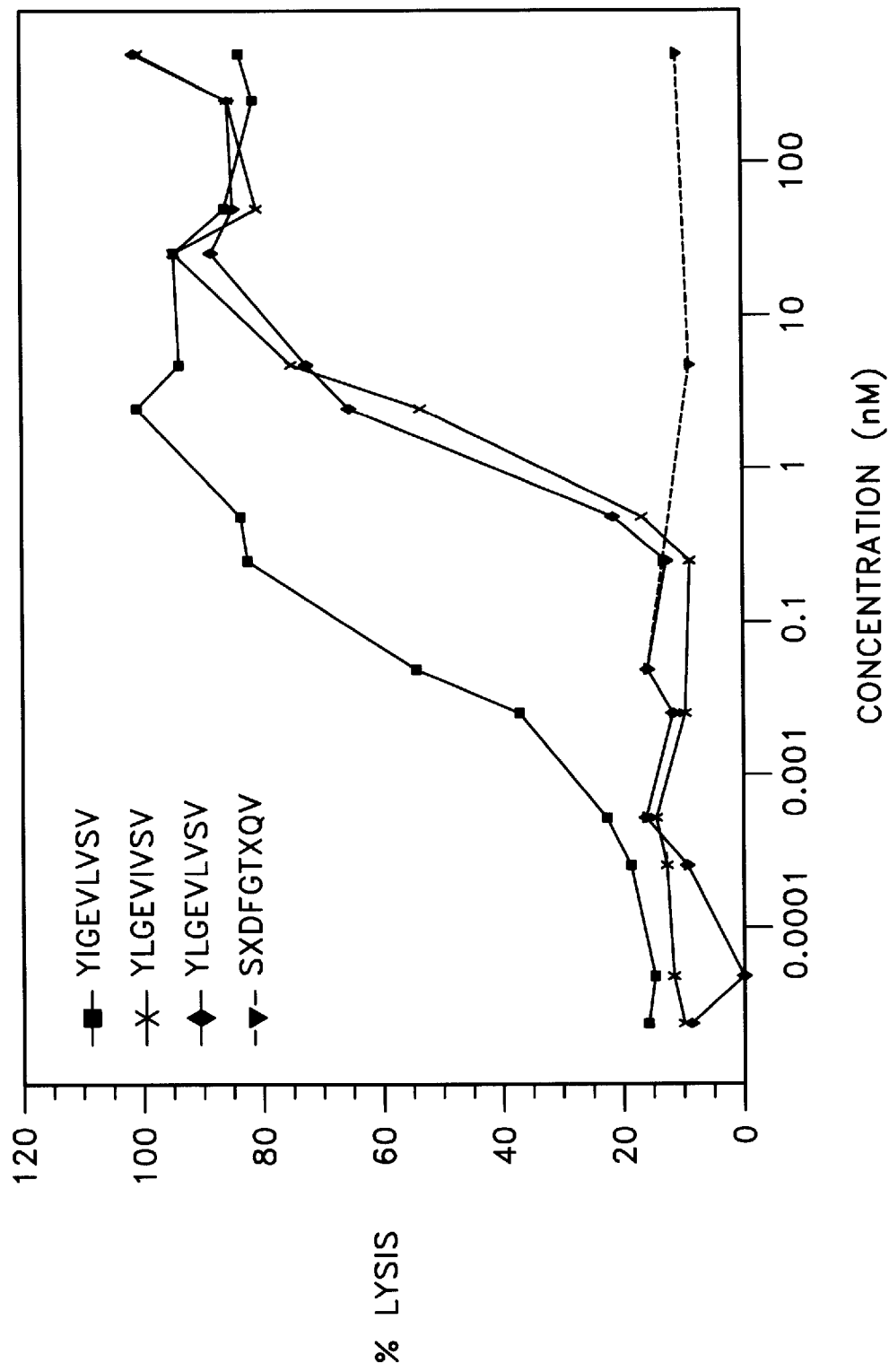

FIG-4B

HA-2 ANTIGENIC PEPTIDE

This invention relates to the field of immunology, especially cellular immunology. It particularly relates to the area of transplantation of organs, tissues or cells (especially bone marrow) and possible immunological reactions caused by such transplantations, Bone marrow transplantation (BMT) finds its clinical application in the treatment of, for instance, severe aplastic anaemia, leukaemia and immune deficiency disease.

In the early days many of these transplantations resulted in rejection of the transplant or in Graft versus Host Disease (GvHD). It is nowadays clear that these effects are largely due to the presence of major H antigens which function as a major transplantation barrier. Consequently, improved success in bone marrow transplantation was reported when matching for the HLA antigens was taken into account. Nowadays, mainly HLA-identical siblings or HLA-matched unrelated individuals are used as a source for the donor material. Still, despite the improvements in HLA-matching, as well as improvements in pretransplantation chemotherapy and/or radiotherapy and the use of potent immunosuppressive drugs as prophylaxis, as well as better antibiotics and better isolation techniques for the donor material, about 20–70% (depending on their age) of the recipients still suffer from GvHD. In GvHD immunocompetent donor T cells react against the host tissues. Therefore donation of marrow from which the mature T cells have been removed has become a frequently used regimen. However, this often leads to graft rejection or failure, as well as to recurrence of the original disease, which is particularly dramatic in leukaemia.

The problems still associated with (particularly) human transplantation can hardly be attributed to the major H antigens, since the donor and recipient are routinely screened for HLA identity. Therefor GvHD may be caused by the disparity of the products of the so called 'minor' H systems (mHag), i.e. Histocompatibility antigens other than those encoded by the MHC.

mHag's have been originally discovered in tumour- and skin rejection studies between congeneic strains of mice. Over 40 mHag loci have been defined, dispersed over the genome, but estimations predict the existence of several hundred loci. One of the better known minor H antigens is the HY antigen.

Several reports have demonstrated the presence of anti-host mHag specific CTL in patients suffering from GvHD after HLA genotypically identical BMT (1–7). In our laboratory, much effort was put into the further characterization of a (small) number of anti-host mHag specific CTLs. Hereto, CTL clones specific for host mHag were isolated from the peripheral blood (PBL) of patients suffering from severe GvHD (8).

Subsequent immunogenetic analyses revealed that the CTL clones (as described above) identified five non-sexlinked mHag, designated HA-1, -2, -3, -4, -5, which are recognized in classical MHC restricted fashion (8). mHag HA-3 is recognized in the presence of HLA-A1 and mHag HA-1, -2, -4 and -5 require the presence of HLA-A2. Segregation studies demonstrated that each of mHag HA-1 to HA-5 is the product of a single gene segregating in a Mendelian fashion and that HA-1 and HA-2 are not coded within the HLA region (9). The mHag differ from each other in phenotype frequencies; mHag HA-2 appeared very frequent (i.e. 95%) in the HLA-A2 positive healthy population (10).

With regard to the mHag expressed on different tissues, we observed ubiquitous versus restricted tissue distribution of the mHag analysed (11). The expression of the mHag HA-2 is restricted to the cells of the haematopoietic cell lineage, such as thymocytes, peripheral blood lymphocytes, B cells and/or monocytes. Also the bone marrow derived professional antigen presenting cells; the dendritic cells and the epidermal Langerhans cells express the mHag HA-2 (11, 12). The mHag HA-2 is also expressed on haematopoietic stem cells (13), on clonogenic leukemic precursor cells (14), as well as on freshly isolated myeloid and lymphoid leukemic cells (15).

To substantiate the importance of the human mH antigenic systems, we investigated whether the mHag are conserved in evolution between human and non human primates. Therefore, cells from non human primates were transfected with the human HLA-A2.1 gene. Subsequent analyses with our human allo HLA-A2.1 and four mHag HLA-2.1 restricted CTL clones revealed the presentation of ape and monkey allo and mHag HY, HA-1 and HA-2 peptides in the context of the transfected human HLA-A2.1 molecule by ape and monkey target cells. Furthermore, peptides were eluted from HLA-A2.1 molecules expressed on the transfected ape cells. An HA-2 positive fraction was identified that showed the same behaviour on reverse phase HPLC as the HA-2 fraction derived from human EBV-LCL. This implies that the HA-2 peptide has been conserved for at least 35 million years (16).

A prospective study was performed in order to document the effect of mHag in HLA genotypically identical BMT on the occurrence of acute (grade$\geq$2) GvHD. The results of the mHag typing using the CTL clones specific for five well defined mHag HA-1 to HA-5 demonstrated a significant correlation between mHag HA-1, -2, -4 and -5 mismatch and GvHD (17).

We aimed at the biochemical characterisation of human mH antigens. Thereto, we made use of the immunopurification and biochemical techniques succesfully applied by Rammensee and his colleagues (18, 19) to extract murine mH peptides from MHC molecules. Indeed, HPLC separation of low Mr molecules (<kD) obtained from acid treated MHC class 1 HLA-A2.1 molecules appeared successful. Fractions with sensitizing activity for the non-sexlinked mH antigen HA-2 specific CTL clones were isolated (20). To analyse the peptidic nature of the mHag HA-2, two sets of experiments were carried out, First, the sensitizing activity of the mHag-containing fractions, obtained as described above, is susceptible to protease treatment; i.e. incubation of these mHag-containing HPLC fractions with pronase or proteinase K abolished the sensitizing activity (21). Second, the MHC encoded TAP1 and TAP2 gene products are required for mHag peptide presentation on the cell surface, The transporter genes TAP1 and TAP2 associated with antigen presentation are required for delivery of peptides from the cytosol with the endoplasmic reticulum (22). The availability of a human cell line "T2" lacking both transport and proteasome subunit genes enabled us to study the processing and presentation of human mH antigens. We demonstrated that the (rat) transport gene products TAP1 and TAP2 were required for processing and presentation of antigenic peptides from influenza virus and from the intracellular mH protein HA-2 (23).

However, until the present invention no one has succeeded in identifying amino acid sequences of antigenic peptides relevant in the mHag system, nor has anyone succeeded in the identification of the proteins from which they are derived. We have now for the first time identified a peptide which is a relevant part of mHag HA-2.

Thus this invention provides a (poly)peptide comprising a T-cell epitope obtainable from the minor Histocompatibility antigen HA-2 comprising the sequence YXGEVXVSV (SEQ ID NO: 1) or a derivative thereof having similar immunological properties, wherein X represents a leucine or an isoleucine residue.

The way these sequences are obtained is described in the experimental part. An important part of this novel method of arriving at said sequences is the purification and the choice of the starting material. Said novel method is therefore also part of the scope of this invention. However, now that the sequence is known, it is of course no longer necessary to follow that method, because the peptides can easily be made synthetically, as is well known in the art. Since routine techniques are available for producing synthetic peptides, it is also within the skill of the art to arrive at analogs or derivatives of the explicitly described peptides, which analogs and/or derivatives may have the same or at least similar properties and or activity. On the other hand analogs which counteract the activity of the explicitly described peptides are also within the skill of the art, given the teaching of the present invention. Therefor derivatives and/or analogs, be it of the same or different length, be it agonist or antagonist, be it peptide-like or peptidomimetic, are part of the scope of this invention.

A preferred embodiment of the present invention is the peptide with the sequence YIGEVLVSV (SEQ ID NO: 2) which induces lysis of the cell presenting it at a very low concentration of peptide present. This does not imply that peptides inducing lysis at higher concentrations are not suitable. This will for a large part depend on the application and on other properties of the peptides, which were not all testable within the scope of the present invention.

The peptides and other molecules according to the invention find their utility in that they may be used to induce tolerance of the donor immune system in HA-2 negative donors, so that residual peripheral blood lymphocytes in the eventually transplanted organ or the bone marrow, as it may be does not respond to host HA-2 material in a HA-2 positive recipient. In this way GvHD may be prevented. On the other hand tolerance may be induced in HA-2 negative recipients in basically the same way, so that upon receipt of an organ or bone marrow from an HA-2 positive donor no rejection on the basis of the HA-2 material occurs. It may be the case that the HA-2 peptide acts in a non-allelic restricted manner. In that case the tolerance induction is not restricted to HA-2 negative individuals.

For tolerance induction very small doses can be given repeatedly, for instance intravenously, but other routes of administration may very well be suitable too. Another possibility is the repeated oral administration of high doses of the peptides. The peptides may be given alone, or in combination with othe peptides, or as part of larger molecules, or coupled to carrier materials in any suitable excipients.

Further applications of the peptide or derivatives thereof lie in the prophylactic administration of such to transplanted individuals to prevent GvHD. This can be done with either agonists, possibly in combination with an adjuvant, or with antagonists which may block the responsible cells. This can be done with or without the concomittant administration of cytokines.

Furthermore the peptides according to the invention can be used to prepare therapeutic agents capable of eliminating a subset of cells, directly or indirectly, especially cells of hematopoietic origin. This can be illustrated by the following examples, which refer to leukemia related therapeutic agents.

a) A HA-2 positive recipient (in bone marrow transplantation) can be subjected to an additional pre bone marrow transplant conditioning regime. This means that an agent which specifically recognizes a peptide according to the invention (a HA-2 peptide) as presented on hematopoietic cells, which agent induces elimination of the cells presenting said peptide, is administered to the recipient before transplantation. This agent will eliminate all residual cells (leukemic cells) of hematopoietic origin, Such agent include but are not limited to T cells (preferably provided with a suicide gene) and/or antibodies coupled to toxic moieties.

b) A HA-2 negative donor for bone marrow transplantation can be vaccinated with a peptide according to the invention, a HA-2 peptide. Upon transplantation to a HA-2 positive recipient, the donor's immune system can eliminate any residual or recurrent HA-2 peptide presenting cells in the recipient which are of course leukemic.

c) A transplanted HA-2 positive recipient, transplanted with HA-2 negative (or for that matter HA-2 positive) bone marrow and suffering from recurrent disease (relapse), i.e. HA-2 positive leukemic cells, can be treated with (again) an agent which specifically recognizes a peptide according to the invention (a HA-2 peptide) as presented on hematopoietic cells, which agent induces elimination of the cells presenting said peptide. In case of HA-2 positive bone marrow being transplanted to the HA-2 positive recipient, it is still essential (in case of recurrent disease) to eliminate all HA-2 positive cells even though this includes the transplanted material, because otherwise the HA-2 positive leukemia will kill the recipient. In the latter case the patient can be retransplanted, if necessary.

Diagnostic applications are clearly within the skill of the art. They include, but are not limited to HA-2 typing, detection of genetic aberrancies and the like.

Other therapeutical applications of the peptide include the induction of tolerance to HA-2 proteins in HA-2 related (auto)immune diseases, such as possibly in Rheumatoid arthritis. On the other hand they may be used in vaccines in HA-2 related (auto)immune diseases.

On the basis of the peptide described herein genetic probes can be produced which can be used to screen for the gene encoding the protein. On the other hand such probes may be useful in detection kits as well. On the basis of the peptide described herein anti-idiotypic B cells and/or T cells and antibodies can be produced. All these embodiments have been made possible by the present disclosure and therefor are part of the present invention.

The techniques to produce these embodiments are all within the skill of the art.

Dose ranges of peptides and antibodies and/or other molecules according to the invention to be used in the therapeutical applications as described hereinbefore are usually designed on the basis of rising dose studies in the clinic. The doses for peptides may lie between about 0.1 and 1000 μg per kg bodyweight, preferably between about 1 and 10 μg per kg bodyweight.

The invention will be described in more explanatory detail in the following experimental part.

EXPERIMENTAL

Using mHag specific CTL clones as in vitro tools, some murine and human mHag have been isolated from MHC molecules by acid elution and were shown to be peptides presented by MHC molecules (13, 14). Further characterization i.e. the exact amino acid sequence of the mHag peptides and the identification of the proteins from which these mHag originate, have so far not been reported. Only a small number of 'non-conventional defined' murine mHag, like the H-3 encoded β2 microglobulin alleles (15) and the Hmt restricted mitochondrial encoded maternally transmitted antigen (16), have been characterized. Here we report the identification, by tandem mass spectrometry, of the HLA-A2.1 restricted mHag HA-2 epitope.

To isolate the mHag HA-2, HLA-A2.1 molecules were purified by affinity chromatography from HLA-A2.1 positive Epstein Barr Virus (EBV)-transformed B lymphocytes (EBV-BLCL) expressing HA-2. The HLA-A2.1 bound peptides were isolated by acid treatment followed by 10 kD filtration (14). These low molecular mass molecules were fractionated by reverse phase HPLC and individual fractions were analyzed for mHag HA-2 sensitizing activity by incubation with the mHag HA-2 negative, HLA-A2.1 positive lymphoblastoid cell-line T2 in a $^{51}Cr$ release assay. One fraction (fraction 33) sensitized T2 for lysis by the HA-2 specific CTL clone 5H17 (17) (FIG. 1a). When this fraction was rechromatographed using a shallower gradient, HA-2 sensitizing activity was observed in fractions 37 and 38 (FIG. 1b). However, as assessed using microcapillary HPLC/electrospray ionisation tandem mass spectrometry, the latter fractions still contained over 100 different HLA-A2 binding peptides (18). To determine which of the peptides was responsible for the HA-2 sensitizing activity, fraction 37 was analyzed using an on-line splitter (19), allowing comparison of the mass spectrometric data with results of the functional assay. FIG. 2b shows a single peak of HA-2 sensitizing activity in four adjacent wells. From the many peptides present in these wells, the relative ion abundance profile of four peptides (with mass to charge ratios (m/z) of 651, 869, 979, 1000) matched the activity profile of the HA-2 Specific CTL activity. Collision activated dissociation (CAD) analysis performed for the species with m/z 979 revealed the existence of 2 different peptides, YXGEVXVSV (SEQ ID NO: 1) and SXDFGTXQV (SEQ ID NO: 3) (FIGS. 3a and 3b). The X stands for L or I, which cannot be distinguished by mass spectrometry under these conditions. Synthetic peptide mixtures were made with an equimolar mixture of L and I in place of X and assayed for HA-2 specific sensitizing CTL activity. Only incubation with peptide mixture YXGEVXVSV (SEQ ID NO: 1) resulted in lysis of T2 (20).

In order to further define the natural processed peptide, four single peptides were synthesized with I or L at positions two and six and microcapillary HPLC coelution studies of these synthetic peptides and the isolated fraction were performed. Peptide YIGEVIVSV (SEQ ID NO: 4) did not coelute with the natural processed peptide and can therefore be excluded as the natural processed epitope, whereas the other three peptides, YIGEVLVSV (SEQ ID NO: 2), YLGEVLVSV (SEQ ID NO: 5) and YLGEVIVSV (SEQ ID NO: 6) did coelute (21). These three peptides all sensitized the T2 cell line for lysis by clone 5H17 (FIG. 4a). Peptide YIGEVLVSV (SEQ ID NO: 2) induced 50% lysis at a concentration of 40 pM, whereas these concentrations were substantially higher for peptides YLGEVLVSV (SEQ ID NO: 5) and YLGEVIVSV (SEQ ID NO: 6) (1.5 nM and 2.25 nM). All three concentrations are within the range of 10 pM–50 nM established for other naturally processed epitopes (19, 22). Clone 5H13 is an independently derived CTL that, based on panel analysis, also recognizes HA-2, but differs slightly in its fine specificity of antigen recognition from 5H17 (10, 23). Clone 5H13 also recognized all 3 peptide variants (FIG. 4b). While the concentration of peptides necessary to give half-maximal epitope reconstitution were 5–10 fold higher than for 5H17, peptide YIGEVLVSV (SEQ ID NO: 2) still sensitized at 100 fold lower concentrations than the other two. These results establish that, despite their fine specificity differences (10, 23), both HA-2 specific CTL recognize the same peptide epitome.

Binding studies with these three peptides showed that peptide YIGEVLVSV (SEQ ID NO: 2) was the highest binder to HLA-A2.1. The concentration that resulted in 50% inhibition of the binding of the iodinated standard peptide to purified HLA-A2.1 was 5.6 nM, while those for YLGEVIVSV (SEQ ID NO: 6) and YLGEYLVSV (SEQ ID NO: 5) were 9.5 and 15 nM respectively (FIG. 5). These values place these peptides among the highest affinity naturally processed peptides that have been defined so far (24). However, the differences in binding affinities for these three peptides is merely a factor of 3. The fact that YIGEVLVSV (SEQ ID NO: 2) sensitizes for recognition by clones 5H17 and 5H13 at 50–100 fold lower concentrations than the other two peptides indicates that this peptide is recognized with highest affinity by the TCR and thus may be the actual HA-2 epitope.

A search of DNA and protein sequence databases led to two human sequences that both matched at 7 out of 9 residues to peptide YIGEVLVSV (SEQ ID NO: 2). Peptide YYGEVCVSV (SEQ ID NO: 7) is derived from oligodendrocyte myelin glycoprotein (25) and peptide YIGSVLISV (SEQ ID NO: 8) was from unconventional myosin IC (26). Both human peptides were synthesized and tested for sensitizing activity. Only the myosin IC derived peptide YIGSVLISV (SEQ ID NO: 8) could sensitize T2 cells for lysis by 5H17 and 5H18 with a 50% lysis inducing concentration of 5–50 nM (27). Human unconventional myosin IC belongs to a large family of myosin genes (28, 29), that consist of different classes and that are indicated to be involved in cell locomotion and organelle transport (28, 29). All cell types probably express several myosins from each class simultaneously. Tissue restricted distribution of some myosins has been reported (26, 29). Database searches showed that in different class I myosins of various origin, ranging from *Acanthamoeba castellanii* to human, this peptide sequence showed conservation for Y, I, G, V, and V at position 1, 2, 3, 5 and 9. Notably, the HA-2 peptide sequence differs in the nonconserved amino acid positions from the myosin IC peptide sequence. Human unconventional myosin IC is the only cloned human class I myosin gene, but there is evidence for the presence of at least 2 other class I myosins in human cells. Therefore, it is not unlikely that an as yet unknown class I myosin protein containing YIGEVLVSV (SEQ ID NO: 2) is present in humans. Interestingly, ongoing studies demonstrate the evolutionary conservation of several mHag, including HA-2, between human and non-human primates (30). Because mHag HA-2 is only presented by haematopoietic cells, this unknown class I myosin is either restricted to haematopoietic cells or is only presented by haematopoietic cells because of tissue specific processing.

The polymorphism of mHag HA-2 is an intriguing issue. 95% of the HLA-A2.1 positive population expresses the HA-2. Consequently, the HA-2 specific CTL were generated in vivo between a mHag HA-2 disparate bone marrow donor/recipient combination. The HA-2 polymorphism can be explained by either mutations in or adjacent to the HA-2 gene or by polymorphism of the antigen processing system.

Until now, information on mHag has been extremely scarce. Although the physiological function of mHag is still unknown, their pivotal role in organ transplantation in general, and in bone marrow transplantation in particular, is undeniable. We herewith report, to our knowledge for the first time, the amino acid sequence of a mHag defined by GvHD-derived CTL. The availability of the mHag peptide sequence may allow in vivo modification of the GvHD related T cell responses. Furthermore, since mHag HA-2 is expressed on cells of the hematopoietic lineage including leukemic cells, it is a candidate for immunotherapy of leukemia prior to bone marrow transplantation.

BRIEF DESCRIPTION OF THE DRAWINGS

FIG. 1a is a graph illustrating the relative mHag HA-2 sensitizing activity of HPLC fractions in a $^{51}$Cr release assay.

Figure 4B:
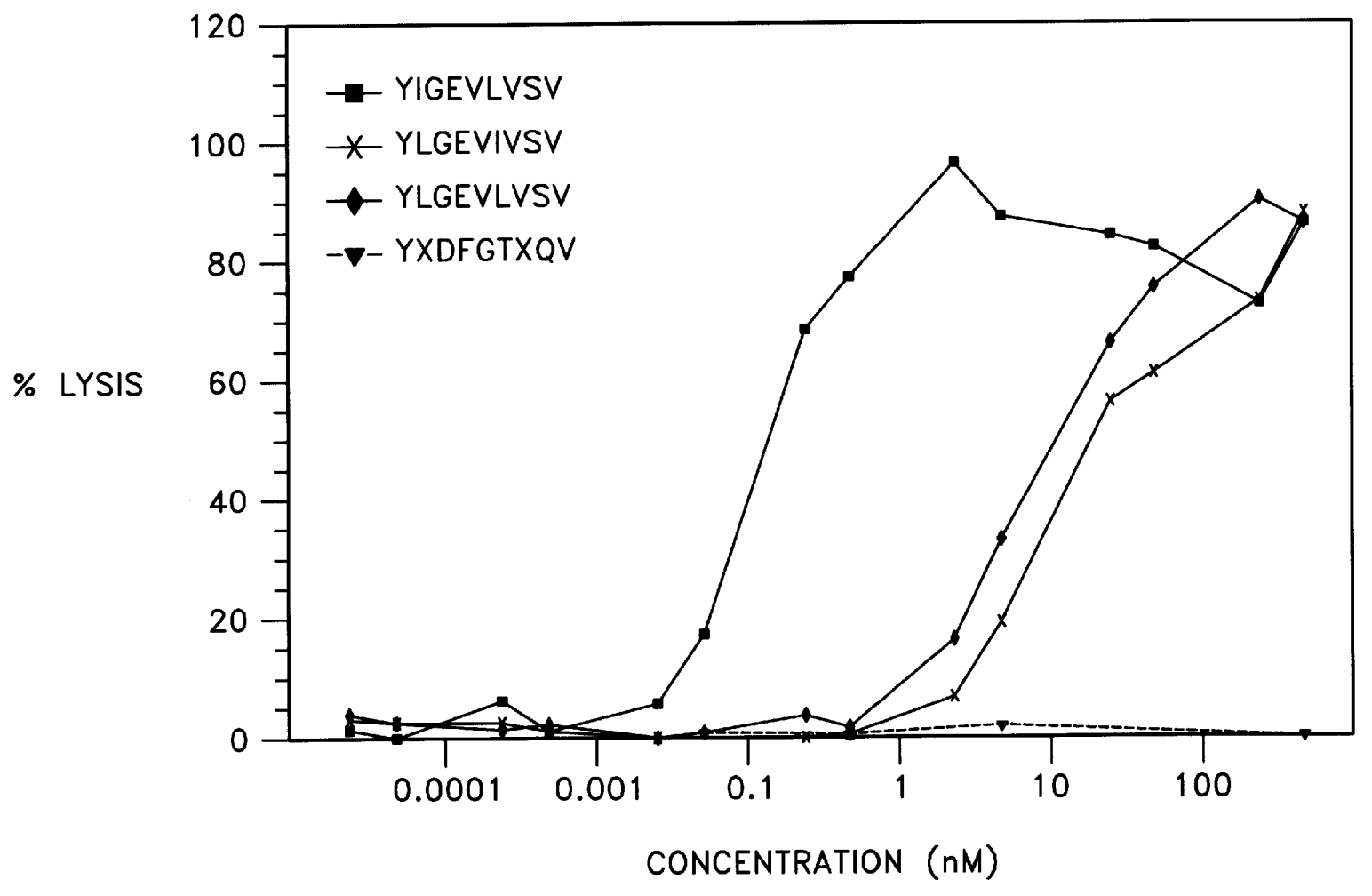

FIG. 4a is a graph showing the dose-dependent activity measured as percent lysis in a cytotoxicity assay (5H17 cytotoxic lymphocytes) for four related synthetic peptides; FIG. 4b is a graph showing the dose-dependent activity measured as percent lysis in a cytotoxicity assay (5H13 cytotoxic lymphocytes) for the four related synthetic peptides.

Figure 1B:
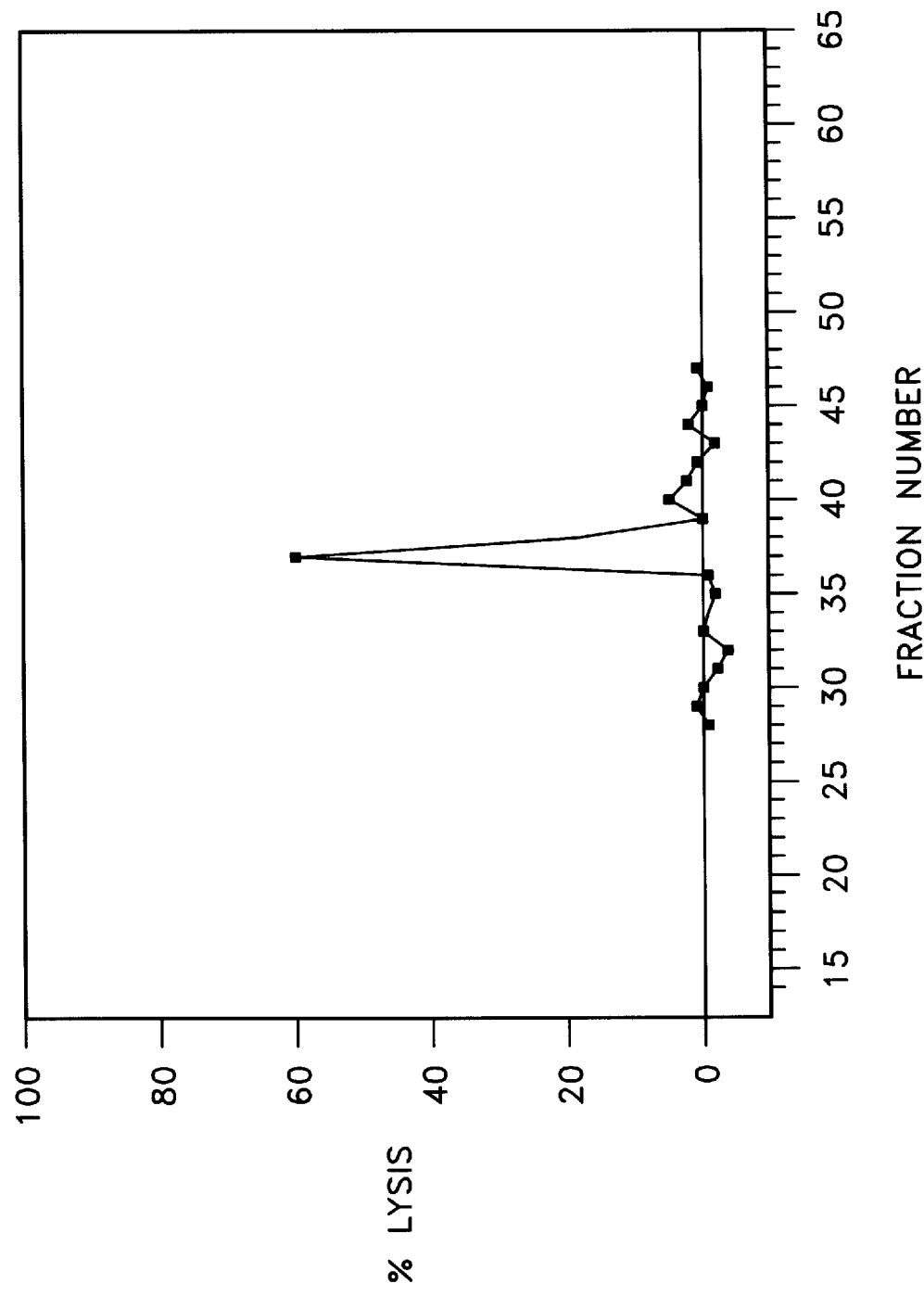
FIG. 1b is a graph illustrating the relative mHag HA-2 sensitizing activity of shallower-gradient HPLC fractions in a $^{51}$Cr release assay.
Figure 2A:
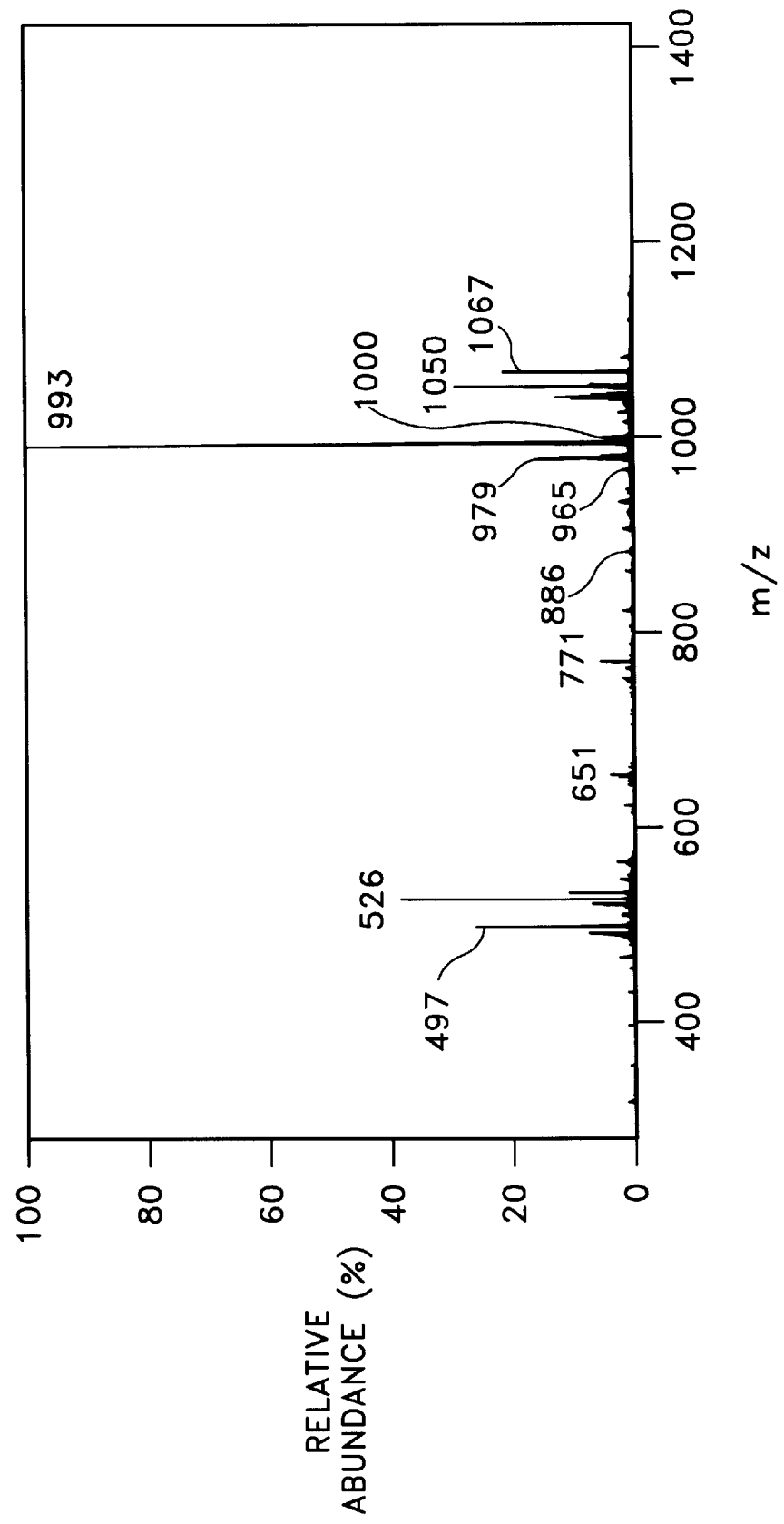
FIG. 2a is a mass spectrogram showing relative abundance of peptides as a function of mass-to-charge ratio (m/z)
Figure 2B:
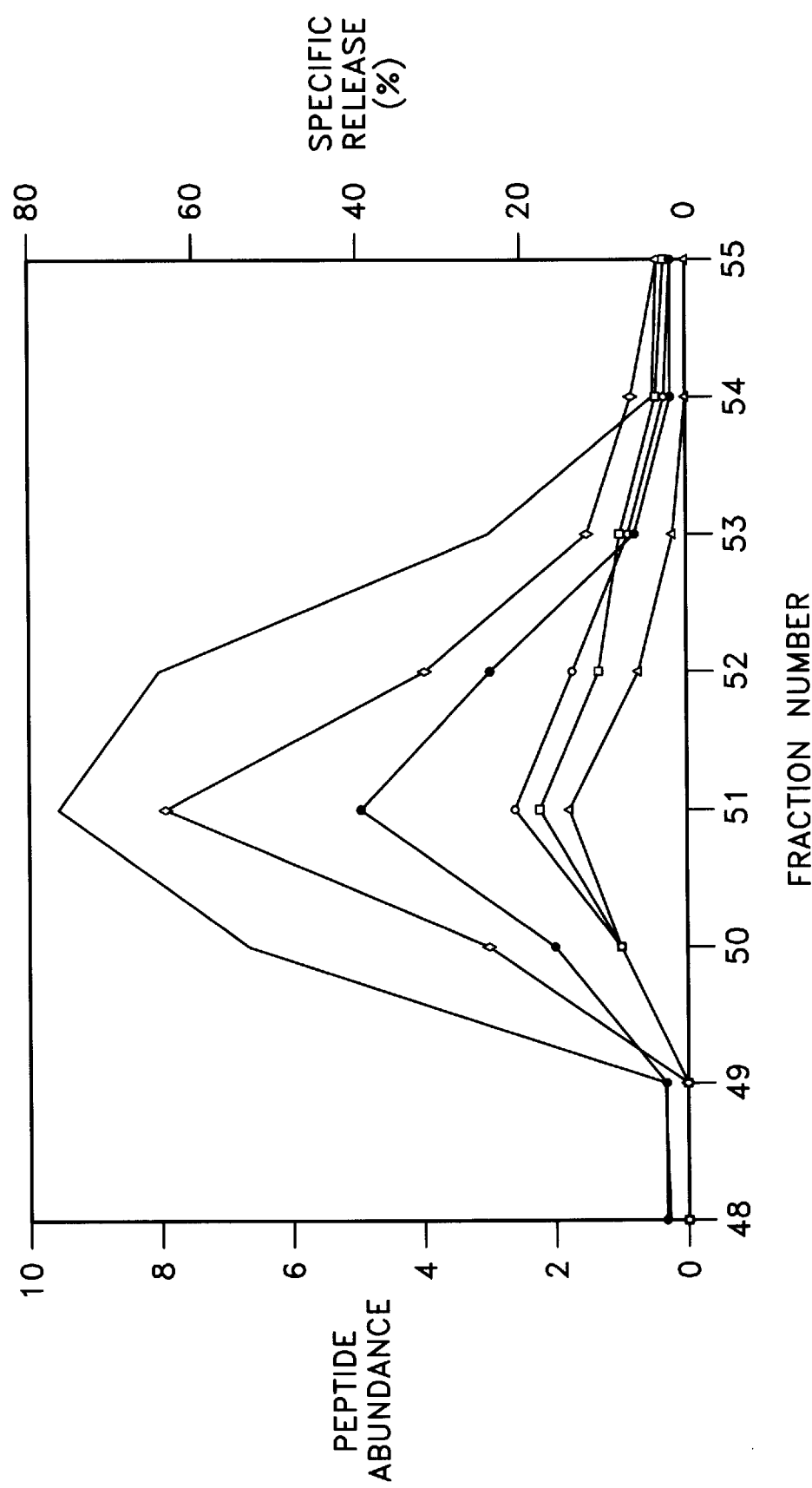
FIG. 2b is a graph showing the comparative HA-2 sensitizing activity of four HA-2-related peptides isolated by mass spectrometry.
Figure 3A:
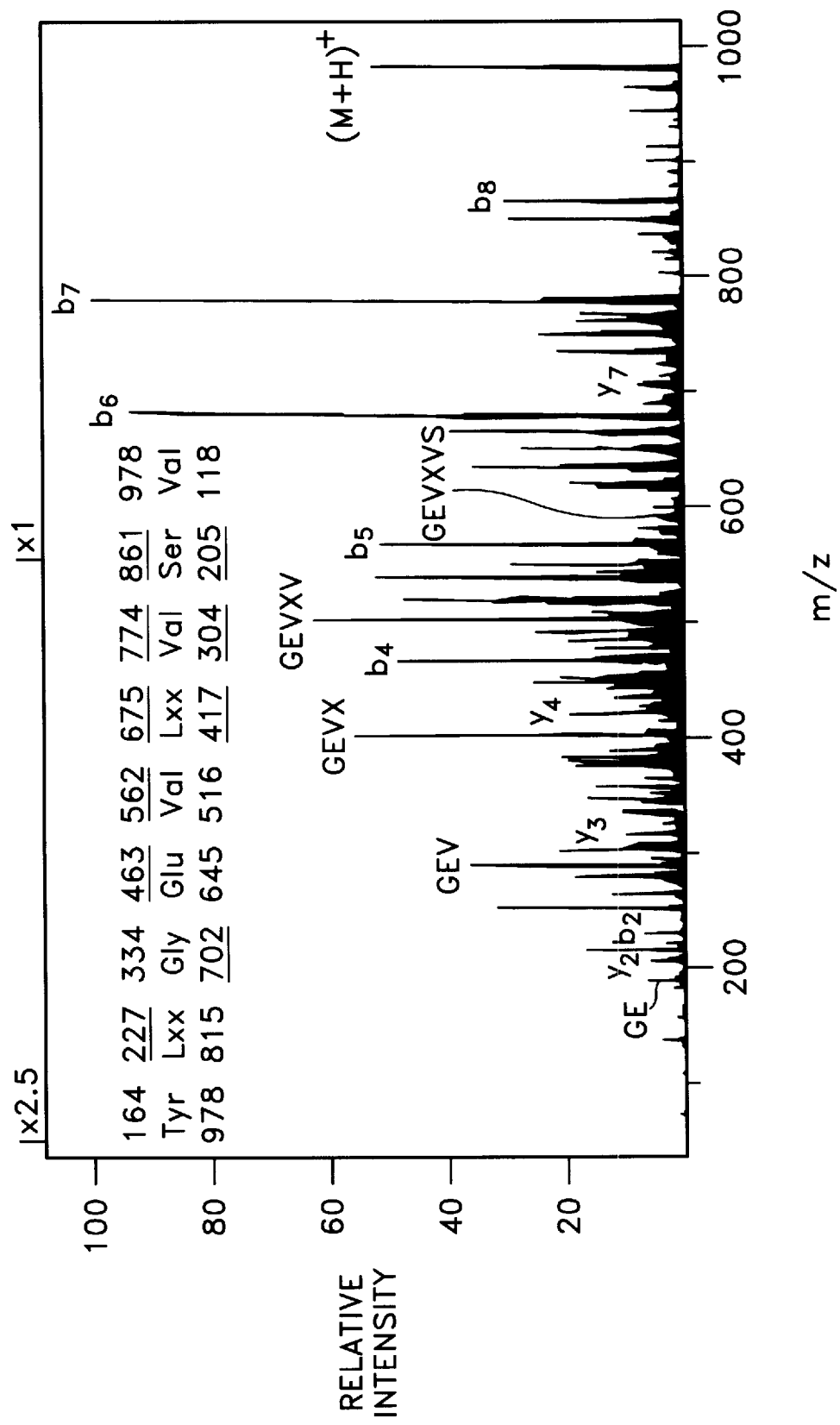
FIG. 3a is a mass spectrogram showing a collision activated dissociation analysis of species with m/z 979 showing a peptide having a sequence identified as SEQ ID NO: 1.
Figure 3B:
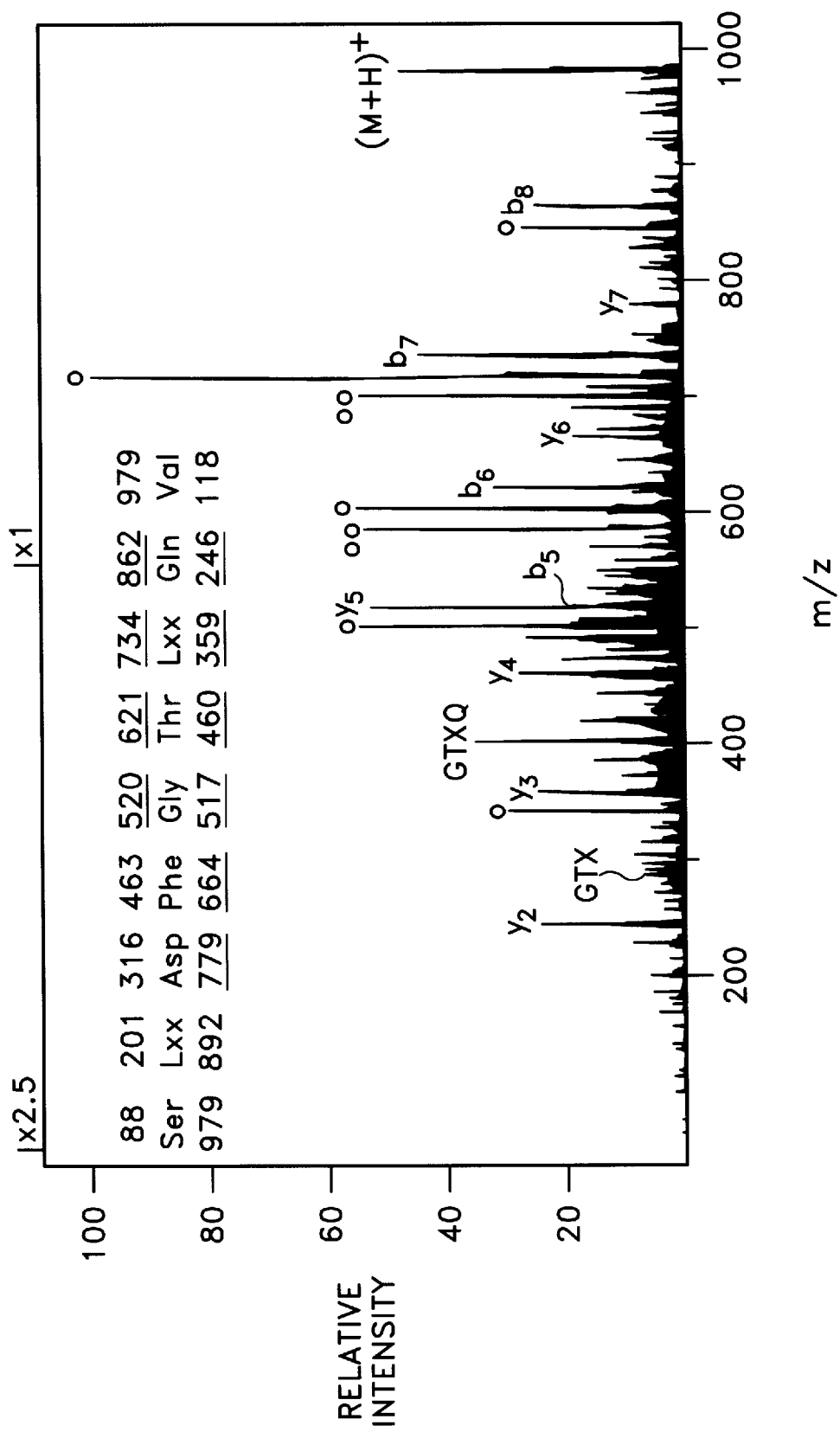
FIG. 3b is a mass spectrogram showing a collision activated dissociation analysis of species with m/z 979 showing a peptide having a sequence identified as SEQ ID NO:3.
Figure 5:
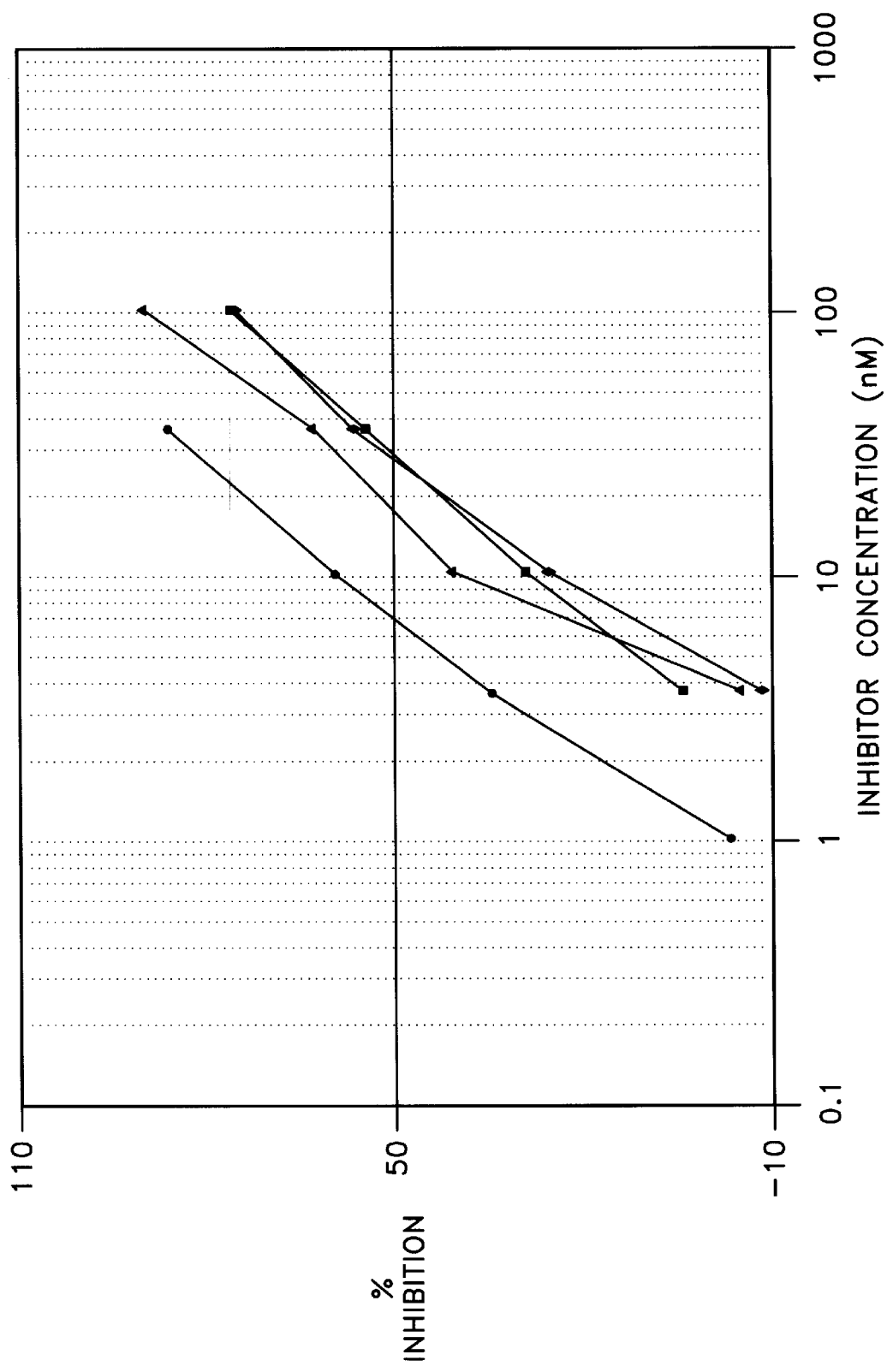
FIG. 5 is a graph showing binding of synthetic peptides to purified HLA-A2.1. HPLC purified peptides were assayed for the ability to inhibit the binding of iodinated hepatitis B core antigen peptide. FLPSDYFPSV (SEQ ID NO: 9), to purified HLA-A2.1 molecules as previously described (23). (closed circles), YIGEVLVSV (SEQ ID NO:2); (closed triangles), YLGEVLVSV (SEQ ID NO:5); (closed squares), YLGEVIVSV (SEQ ID NO:6); (closed diamonds), the influenza M1 protein antigen GILGFVFTL (SEQ ID NO:1). All data points are the average of at least two independent experiments.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: variable residue
        ( B ) LOCATION: 2
        ( C ) OTHER INFORMATION: /note= a leucine or an isoleucine residue ( i x ) FEATURE:
        ( A ) NAME/KEY: variable residue
        ( B ) LOCATION: 6
        ( C ) OTHER INFORMATION: /note= a leucine or an isoleucine residue ( x i ) SEQUENCE DESCRIPTION: SEQ ID NO:1:

Tyr  Xaa  Gly  Glu  Val  Xaa  Val  Ser  Val
1                              5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Tyr  Ile  Gly  Glu  Val  Leu  Val  Ser  Val
1                              5

( 2 ) INFORMATION FOR SEQ ID NO:3:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: variable residue
    ( B ) LOCATION: 2
    ( C ) OTHER INFORMATION: /note= a leucine or an
      isoleucine residue ( i x ) FEATURE:
    ( A ) NAME/KEY: variable residue
    ( B ) LOCATION: 7
    ( C ) OTHER INFORMATION: /note= a leucine or an
      isoleucine residue ( x i ) SEQUENCE DESCRIPTION: SEQ ID NO:3:

Ser Xaa Asp Phe Gly Thr Xaa Gln Val
1         5

( 2 ) INFORMATION FOR SEQ ID NO:4:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Tyr Ile Gly Glu Val Ile Val Ser Val
1         5

( 2 ) INFORMATION FOR SEQ ID NO:5:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Tyr Leu Gly Glu Val Leu Val Ser Val
1         5

( 2 ) INFORMATION FOR SEQ ID NO:6:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

Tyr Leu Gly Glu Val Ile Val Ser Val
1         5

( 2 ) INFORMATION FOR SEQ ID NO:7:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:7:

Tyr Tyr Gly Glu Val Cys Val Ser Val
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Tyr Ile Gly Ser Val Leu Ile Ser Val
1               5

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Phe Leu Pro Ser Asp Tyr Phe Pro Ser Val
1               5                   10

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Gly Ile Leu Gly Phe Val Phe Thr Leu
1               5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: variable residue
        ( B ) LOCATION: 6
        ( C ) OTHER INFORMATION: /note= a leucine or an
                isoleucine residue ( x i ) SEQUENCE DESCRIPTION: SEQ ID NO:11:

Tyr Ser Gly Glu Val Xaa Val Ser Val
1               5

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( D ) TOPOLOGY: linear (ii) MOLECULE TYPE: peptide (ix) FEATURE:
  (A) NAME/KEY: variable residue
  (B) LOCATION: 2
  (C) OTHER INFORMATION: /note= a leucine or an isoleucine residue (ix) FEATURE:
  (A) NAME/KEY: variable residue
  (B) LOCATION: 7
  (C) OTHER INFORMATION: /note= a leucine or an isoleucine residue (xi) SEQUENCE DESCRIPTION: SEQ ID NO:12:

Tyr Xaa Asp Phe Gly Tyr Xaa Gln Val
1               5

REFERENCES

1. Goulmy E, Gratama J W, Blokland E, Zwaan F E, van Rood J J. (1983) A minor transplation antigen detected by MHC restricted cytotoxic T lymphocytes during graft-versus-host-disease. *Nature* 302:159–161.
2. Tsoi M-S, Storb R, Dobbs S, Medill I, Thomas E D. (1980) Cell mediated immunity to non-HLA antigens of the host by donor lymphocytes in patients with chronic graft-vs-host disease. *J. Immunol.* 125:2258–2262.
3. Tsoi M-S, Storb R, Santos E, Thomas E D. (1983) Anti-host cytotoxic cells in patients with acute graft-versus-host disease after HLA identical marrow grafting. *Transplant Proc.* 15:1484–1486.
4. Irlè C, Beatty P G, Mickelson E, Thomas ED, Hansen J A. (1985) Alloreactive T cell responses between HLA identical siblings. *Transplantation* 40:329–333.
5. Van Els C, Bakker A, Zwinderman A H, Zwaan F E, van Rood J J, Goulmy E. (1990) Effector mechanisms in GvHD in response to minor Histocompatibility antigens. I. Absence of correlation with CTLs. *Transplantation* 50:62–66.
6. Irscheck E, Hladik T, Niederwieser D et al. (1992) Studies on the mechanism of tolerance or Graft-versus-Host Disease in allogenic bone marrow recipients at the level of cytotoxic T cell precursor frequencies. *Blood* 79:1622–1628.
7. Niederwieser D, Grassegger A, Auböck J, Herold M, Nachbaur D, Rosenmayr A, Gächter A, Nussbaumer W, Gaggl S, Ritter M and Huber C. (1993) Correlation of minor histocompatibility antigen specific cytotoxic T lymphocytes with Graft-versus-Host Disease status and analyses of tissue distribution of their target antigens. *Blood* 81:2200–2208.
8. Goulmy E. (1985) Class-I restricted human cytotoxic T lymphocytes directed against transplantation antigens and their possible role in organ transplantation. *Prog. in Allergy* 36:44–72.
9. Schreuder G M T H, Pool J, Blockland E, Van Els C, Bakker A, Van Rood J J and Goulmy E. (1993) Genetic analysis of human minor Histocompatibility antigens demonstrates Mendelian segregation independent from HLA. *Immunogenetics* 38:98–105.
10. Van Els C, D'Amaro J, Pool J, Bakker A, van den Elsen P J, Van Rood J J and Goulmy E. (1992) Immunogenetics of human minor Histocompatibility antigens: their polymorphism and immunodominance. *Immunogenetics* 35:161–165.
11. De Bueger M, Bakker A, Van Rood J J, Van der Woude F and Goulmy E. (1992) Tissue distribution of human minor Histocompatibility antigen. Ubiquitous versus restricted tissue distribution indicates heterogeneity among human CTLs defined non-MHC antigens *J. Immunology* 149:1788–1794.
12. Van Lochem E G, Van de Keur M, Mommaas M, de Gast G and Goulmy E. (1994). Expression of cytotoxic T cell defined minor Histocompatibility antigens on human peripheral blood dendritic cells and skin derived Langerhans cells. Manuscript submitted for publication.
13. Marijt W A F, Veenhof W F J, Goulmy E, Willemze R, Van Rood J J and Falkenburg J H F. (1993) Minor histocompatibility antigen HA-1, -2, -4 and HY specific cytotoxic T cell clones inhibit human hematopoietic progenitor cell growth by a mechanism that is dependent on direct cell-cell contact. *Blood* 82:3778–3785.
14. Falkenburg F, Goselink H, van der Harst D, Van Luxemburg-Heijs SAP, Kooy-Winkelaar Y M C, Faber L M, de Kroon J, Brand A, Fibbe W E, Willemeze R and Goulmy E. (1991) Growth inhibition of clonogenic leukemic precursor cells by minor histocompatibility antigen-specific cytotoxic T lymphocytes. *J. Exp. Med.* 174:27–33.
15. Van der Harst D, Goulmy E, Falkenburg J H F et al. (1994) Recognition of minor histocompatibility antigens on lymphocytic and myeloid leukemic cells by cytotoxic T-cell clones. Blood 83:1060–1066.
16. Den Haan J, Pool J, Blockland E, Bontrop R and Goulmy E. (1994) Minor Histocompatibility antigens are conserved between primates. Manuscript in preparation.
17. Goulmy E, Schipper R, Pool J. (1994) Minor histocompatibility antigen mismatches influence the development of GvHD after HLA genotypically identical bone marrow transplantation. Manuscript submitted for publication.
18. Rötzschke O, Falk K, Wallny H-J, Faath S and Rammensee H-G. (1990) *Science* 249:283.
19. Falk K, Rötzschke O and Rammensee H-G. (1990) *Nature* 348:248.
20. De Bueger M, Verreck F, Blokland E, Drijfhout J-W, Amons R, Koning F and Goulmy E. (1993) Isolation of a HLA-A2.1 extracted human minor histocompatibility peptide. *Eur. J. Immunol.* 23:614–618.
21. Den Haan J J M, Blockland E, Koning F, Drijfhout J-W and Goulmy E. (1994) Structure analysis of human minor histocompatibility antigens HA-1 and HA-2. Abstract NWO retraite.
22. Powis S J, Townsend R M, Deverson E V et al. (1991) *Nature* 354:528.
23. Momburg F. Ortiz-Navarrete V, Neefjes J, Goulmy E, v.d. Wal Y, Spits H, Powis S J, Butcher G W, Howard J C, Walden P and Hämmerling G J. (1992) The proteasome subunits encoded by the major histocompatibility complex are not essential for antigen presentation. *Nature* 360:174–177.
24. Wallny H J and Rammensee H-G. (1990) *Nature* 343:275; Rötzschke O, Falk K, Wallny H J, Faath S, Rammensee H-G. (1990) *Science* 249:283; Sekimata M, Griem P, Egawa K, Rammensee H-G, Takiguchi M. (1992) *Int. Immunol.* 4:301; Franksson L, Petersson M, Kiessling R, Karre K. (1993) *Eur. J. Immunol.* 23:2606.
25. De Buegar M et al. (1993) *Eur. J. Immunol.* 23:614.
26. Kurtz M E, Graff R J, Adelman A, Martin-Morgan D, Click R E. (1985) *J. Immunol.* 135:2847; Rammensee H-G Robinson P J, Grisanti A, Bevan M J. (1986) *Nature* 319:502; Perarnau B et al. (1990) *Nature* 346:751.
27. Loveland B, Wang C-R, Yonekawa H, Hermel E, Fischer-Lindahl K. (1990) Cell 60:971.
28. The HA-2 specific CTL clone 5H17 originate from a female patient who underwent bone marrow transplantation for severe aplastic anaemia. The pre-transplant conditioning regime consisted of total lymphoid irradiation and cyclophosphamide. The patient was grafted with non-T-cell-depleted bone marrow from her HLA identical father. The patient suffered from severe acute GvHD grade III followed by extensive chronic GvHD. The HA-2 specific CTL clone was generated from post BMT PBL according to the protocol described earlier. Goulmy E. (1988) In *Transplant. Rev.* Morris J and Tilney N L, Eds., Saunders Company 2:29.
29. Data not shown.
30. Cox A L et al. (1994) *Science* 264:716.
31. Peptide mixtures YSGEVXVSV and SXDFGTXQV were tested in several concentrations against clone 5H17 and clone 5H13. In addition to T2, an HA-2 negative HLA-A2.1 positive EBV-BLCL was used to present the peptide mixture.
32. Data not shown.
33. Udake K, Tsomides T J, Eisen H N. (1992) *Cell* 69:989; Henderson R A et al. (1993) *Proc. Natl. Acad. Sci. USA* 90:10275; Mandelboim O et al. (1994) *Nature* 369:67; Uenaka A et al. (1994) *J. Exp. Med.* 180:1599.
34. 5H13 and 5H17 demonstrated identical patterns when analyzed against 100 healthy unrelated HLA-A2.1 positive individuals. A discriminatory reaction pattern between the clones was noted when a target cell was analyzed expressing a natural HLA-A2 variant molecule.
35. Chen Y et al. (1994) *J. Immunol.* 152:2874; Ruppert J et al. (1993) *Cell* 74:829.
36.
37. Bement W M, Hasson T, Wirth J A, Cheney R E, Mooseker M S. (1994) *Proc. Natl. Acad. Sci. USA* 91:6549.
38. Peptide YYGEVCVSV was tested in a concentration range of 50 nM to 0.5 pM against 5H17 as well as 5H13. No activity was found.
39. Titus M A. (1993) *Curr. Opin. Cell Biol.* 5:74; Coudrier E, Durrbach A, Louvard D. (1992) *FEBS* 307:87.
40. Mooseker M. (1993) *Curr. Biol.* 3:245.
41. den Haan J M M, Pool J, Blokland E, Bontrop R, Goulmy E. Manuscript in preparation.

What is claimed is:

1. A purified or isolated HA-2 minor histocompatibility antigen polypeptide comprising the amino acid sequence YXGEVXVSV (SEQ ID NO: 1) wherein "X" represents a leucine or isoleucine residue and wherein said polypeptide comprises a T cell epitope.

2. The polypeptide of claim 1 comprising the amino acid sequence YIGEVLVSV (SEQ ID NO:2).

3. The polypeptide of claim 1 comprising one of the following amino acid sequences: YLGEVLVSV (SEQ ID NO: 5) or YLGEVIVSV (SEQ ID NO: 6).

4. A purified or isolated HA-2 minor histocompatibility antigen peptide comprising the amino acid sequence YXGEVXVSV (SEQ ID NO: 1) wherein "X" represents a leucine or isoleucine residue, wherein said peptide comprises a T cell epitope and is capable of being presented by a Class I MHC molecule.

5. A composition comprising a polypeptide of any one of claims 1, 2, 3 or 4 and a physiologically acceptable diluent.

6. A vaccine capable of inducing a Class I MHC-mediated immune response to an HA-2 antigen in an HA-2 negative subject comprising a polypeptide of any one of claims 1, 2, 3 or 4 and a pharmaceutically acceptable carrier or excipient.

7. A method for the elimination of hematopoietic cells presenting an HA-2 minor histocompatibility antigen peptide or polypeptide in a subject comprising administering the vaccine of claim 6 to said subject, wherein said HA-2 peptide or polypeptide comprises the amino acid sequence YXGEVXVSV (SEQ ID NO: 1) and wherein "X" represents a leucine or isoleucine residue.

8. The method of claim 7 wherein said hematopoietic cells are neoplastic cells.

9. The method of claim 7 wherein said Class I MHC-mediated immune response is mediated by HLA-A2.

10. A method for inducing immune tolerance in an allograft comprising administering the vaccine of claim 6 to an HA-2 negative allograft donor prior to transplantation in an amount sufficient to inhibit Graft-vs-Host Disease in a recipient following transplantation.

11. A method for inducing immune tolerance to an allograft comprising administering the vaccine of claim 6 to an HA-2 negative allograft recipient prior to transplantation in an amount sufficient to inhibit allograft rejection in said recipient following transplantation.

* * * * *

UNITED STATES PATENT AND TRADEMARK OFFICE
CERTIFICATE OF CORRECTION

PATENT NO. : 5,770,201
DATED : June 23, 1998
INVENTOR(S) : Goulmy et al.

It is certified that error appears in the above-identified patent and that said Letters Patent is hereby corrected as shown below:

In Column 4, Line 8,      the patent now reads --, Such agent include--;
this should read --. Such agents inlcude--.

In Column 6, Line 12,      the patent now reads --YLGEVIVSV and YLGEYLVSV--;
this should read --YLGEVIVSV and YLGEVLVSV--.

Signed and Sealed this

Ninth Day of February, 1999

*Attest:*

*Attesting Officer*

*Acting Commissioner of Patents and Trademarks*

UNITED STATES PATENT AND TRADEMARK OFFICE
CERTIFICATE OF CORRECTION

PATENT NO. : 5,770, 201
DATED : June 23, 1998
INVENTOR(S) : Goulmy et al.

It is certified that error appears in the above-identified patent and that said Letters Patent is hereby corrected as shown below:

In Column 3, Line 51,    the patent now reads --combination with othe peptides--;
                         this should read --combination with other peptides--.

In Column 6, Line 32,    the patent now reads --by 5H17 and 5H18 with--;
                         this should read --5H17 and 5H13 with--.

Signed and Sealed this

Fourth Day of May, 1999

Attest:

Q. TODD DICKINSON

*Attesting Officer*    Acting Commissioner of Patents and Trademarks